(12) United States Patent
Hill et al.

(10) Patent No.: US 8,734,806 B2
(45) Date of Patent: May 27, 2014

(54) IMMUNOGENIC COMPOSITION AND USE THEREOF

(75) Inventors: Adrian V. S. Hill, Oxford (GB); Arturo Reyes-Sandoval, Oxford (GB)

(73) Assignee: ISIS Innovation Limited, Oxfordshire (GB)

( * ) Notice: Subject to any disclaimer, the term of this patent is extended or adjusted under 35 U.S.C. 154(b) by 231 days.

(21) Appl. No.: 13/140,893

(22) PCT Filed: Dec. 23, 2009

(86) PCT No.: PCT/GB2009/051766
§ 371 (c)(1),
(2), (4) Date: Sep. 13, 2011

(87) PCT Pub. No.: WO2010/073043
PCT Pub. Date: Jul. 1, 2010

(65) Prior Publication Data
US 2012/0076818 A1    Mar. 29, 2012

(30) Foreign Application Priority Data

Dec. 24, 2008  (GB) .................................. 0823497.3

(51) Int. Cl.
*A61K 39/295* (2006.01)
*A61K 39/235* (2006.01)
*A61K 39/275* (2006.01)
*A61K 39/285* (2006.01)

(52) U.S. Cl.
USPC ................... 424/199.1; 435/235.1; 435/320.1

(58) Field of Classification Search
None
See application file for complete search history.

(56) References Cited

U.S. PATENT DOCUMENTS

| | | |
|---|---|---|
| 2003/0138459 A1 | 7/2003 | Wang |
| 2005/0287162 A1 | 12/2005 | Baier et al. |
| 2007/0207166 A1 | 9/2007 | Nabel et al. |
| 2007/0231347 A1* | 10/2007 | Wilson et al. ............. 424/205.1 |
| 2008/0063656 A1* | 3/2008 | Emini et al. ............. 424/188.1 |
| 2008/0220014 A1 | 9/2008 | Pau et al. |

FOREIGN PATENT DOCUMENTS

| | | |
|---|---|---|
| AU | 757683 | 2/2003 |
| CN | 101363028 | 1/2007 |
| EP | 1 737 885 | 1/2007 |
| WO | 01/21201 | 3/2001 |
| WO | 2006/020071 | 2/2006 |
| WO | 2006/033672 | 3/2006 |
| WO | 2007/035455 | 3/2007 |
| WO | 2007/102326 | 9/2007 |
| WO | 2008/122769 | 10/2008 |
| WO | 2008/122811 | 10/2008 |

OTHER PUBLICATIONS

Draper et al (Nature Medicine 14:819-821, Jul. 27, 2008).*
Yashima et al (Vaccine 28:3257-3264, 2010, not prior art).*
Casimiro et al., "Heterologous Human Immunodeficiency Virus Type 1 Priming-Boosting Immunization Strategies Involving Replication-Defective Adenovirus and Poxvirus Vaccine Vectors", Journal of Virology, 78(30):11434-11438 (Oct. 2004).
Reyes-Sandoval et al., "Prime-Boost Immunization with Adenoviral and Modified Vaccinia Virus Ankara Vectors Enhances the Durability and Polyfunctionality of Protective Malaria CD8+ T-Cell Responses", Infection and Immunity, 78(1):145-153 (Jan. 2010).
Anderson et al., "Enhanced CD8+ T Cell Immune Response and Protection Elicited against *Plasmodium berghei* Malaria by Prime Boost Immunization Regimens Using a Novel Attenuated Fowlpox Virus", The Journal of Immunology, 172:3094-3100 (2004).
Draper et al., "Effective induction of high-titer antibodies by viral vector vaccines", Nature Medicine, 14(8):819-821 (Aug. 2008).

* cited by examiner

Primary Examiner — Mary E Mosher
(74) Attorney, Agent, or Firm — Rodney J. Fuller; Booth Udall Fuller, PLC (57) ABSTRACT

The invention relates to an immunogenic composition comprising an adenoviral vector and a pox viral vector, or two different adenoviral vectors, wherein one or more of the vectors encodes one or more target antigens; and related methods, uses and kits.

13 Claims, 10 Drawing Sheets

IMMUNOGENIC COMPOSITION AND USE THEREOF

This application is the U.S. national stage of PCT/GB2009/051766, filed Dec. 23, 2009, which claims priority to and benefit of Great Britain Patent Application No. 0823497.3, filed Dec. 24, 2008, the contents of each of which are herein incorporated by reference for all purposes.

Incorporated by reference in its entirety herein is a computer-readable nucleotide/amino acid sequence listing submitted concurrently herewith and identified as follows: One 618 byte ASCII (text) file named "Seq_List" created on Jun. 20, 2011.

The invention relates to immunogenic compositions and the use of such compositions to generate an improved immune response in a subject.

Over the last 10 to 15 years extensive research and development has been undertaken on the development of "vectored vaccines" which are engineered to express an antigen of interest (AVS Hill, Nat Rev Imm (2006); Shengqiang Li et al, Vaccine (2007) 25:2567; Souza A. D. P. et al, Braz Journal of Medical and Biological Research (2005) 38:509). Most vectored vaccines rely on the induction of antibody responses to proteins expressed by the vectors to protect against infectious agents. However, for some infectious diseases such as HIV, malaria and tuberculosis, vaccine efforts have shifted to the stimulation of T-cell responses that have shown protection per se in both human and mouse models (Reyes-Sandoval et al, Eur J Immunol (2008) 38:732-741; Webster et al, Proc Natl Acad Sci USA (2005) 102:4836-4841). Similarly, there is great interest in the use of T cell inducing vaccines for therapeutic vaccination against cancer, tumours and chronic infectious diseases.

Poxviral vectors, such as MVA and FP9 are at the forefront of malaria and tuberculosis vectored vaccine development (Anderson et al, J Immunol (2004) 172:3094-3100; McShane et al, Nat Med (2004) 10:1240-1244). With respect to malaria, it has been shown that the poxviral vectors MVA and FP9 can induce a certain degree of protection to malaria when administered sequentially as prime-boost regimes (Anderson et al, J Immunol (2004) 172:3094-3100). However, a single administration of such vectors does not confer resistance to malaria in mouse models (Reyes-Sandoval et al, Eur J Immunol (2008) 38:732-741).

More recently, there has been an increased interest in the development of additional viral vectors that could induce more potent T-cell responses. Vectors based on replication-deficient adenovirus have been shown to induce potent antibody responses that protect against rabies (Xiang et al, J Virol (2002) 76:2667-2675). In addition, these vectors have also been shown to stimulate the other arm of the immune response and induce outstanding T-cell responses to HIV in both mice and macaques (Pinto et al, J Immunol (2003) 171:6774-6779; Reyes-Sandoval et al, J Virol (2004) 78:7392-7399). Such adenoviral vectors have also shown for the first time the ability to induce high levels of complete, sterile protection to malaria in a mouse model by a single vaccination (Reyes-Sandoval et al, Eur J Immunol (2008) 38:732-741). In order for adenoviral vectors to confer high protective levels, high concentrations of the viral vectors are required. Such protective levels are short-lived and protection decreases significantly when the challenge is performed after long intervals. Nevertheless, the sequential administration of two different vectors encoding the same antigen spaced by some time, also known as heterologous prime-boost regimes can improve immunogenicity and long-term protection from malaria in mice, especially when an adenoviral vector is first administered followed by an MVA vector. The protective efficacy of such regimes can reach levels of up to 80% complete, sterile protection on the long term (>2 months after the last vaccination) depending on the vector used. There remains however the need for further improvements in the protective efficacy of viral vectored vaccines.

According to a first aspect, the present invention provides an immunogenic composition comprising an adenoviral vector and a pox viral vector, or two different adenoviral vectors, wherein one or more of the vectors encodes one or more target antigens.

The immunogenic composition may be for use as a vaccine.

The two different adenoviral vectors preferably differ in the vector backbone not just in the transgene.

Surprisingly, the administration of an adenoviral and a pox viral vector, or two different adenoviral vectors, where these latter differ in the vector backbone not just in the transgene, to an organism at the same time, or very close together, is remarkably immunogenic and protective. Such mixtures allow the use of lower doses of vectors, and also surprisingly allow the repeated administration of the same vectors, this allows for improved vaccination safety, simpler administration regimes of such vaccines, as well as improved immunogenicity and efficacy profiles.

According to a further aspect, the invention provides a composition comprising an adenoviral vector and a pox viral vector, or two different adenoviral vectors, wherein one or more of the vectors encodes one or more target antigens for use in inducing or amplifying an immune response to one or more target antigens in an organism.

According to a further aspect, the invention provides the use of an adenoviral vector and a pox viral vector, or the use of two different adenoviral vectors, wherein one or more of the vectors encodes one or more target antigens in the preparation of a medicament for use in inducing or amplifying an immune response in an organism, such as a mammal.

According to another aspect, the invention provides a method of inducing an immune response in an organism, such as a mammal, comprising the step of administering to the organism a composition according to one of the preceding aspects of the invention.

According to a yet further aspect, the invention provides a method of inducing an immune response in an organism, such as a mammal, comprising the step of administering to the organism an adenoviral vector and a pox viral vector, or two different adenoviral vectors, wherein one or more of the vectors encodes one or more target antigens.

Where reference if made hearin to "two different adenoviral vectors", the two different adenoviral vectors preferably differ in the vector backbone not just in the transgene.

The adenoviral vector and the pox viral vector, or the two different adenoviral vectors, may be administered as a mixture, or alternatively they may be administered separately. If administered separately the vectors may be administered at the same or different sites. The administration of each vector may be simultaneous, or substantially simultaneous, for example, within 10 minutes of each other, or the administration may be sequential. Preferably if the two vectors are administered sequentially, they are administered within at most about 7 days, 6 days, 4 days, 2 days, 24 hours or less, of each other.

According to yet another aspect, the invention provides a method of inducing an immune response in an organism, such as a mammal, comprising the steps of exposing the organism to a priming composition that comprises an adenoviral vector and a pox viral vector, or two different adenoviral vectors, wherein one or more of the vectors encodes one or more target antigens, and then boosting the immune response by administering a boosting composition comprising an adenoviral vector and a pox viral vector, or two different adenoviral vectors, wherein one or more of the vectors encodes one or more target antigens.

According to a further aspect, the invention provides a method of inducing an immune response in an organism, such as a mammal, comprising the steps of exposing the organism to a priming step that comprises administering to the organism an adenoviral vector and a pox viral vector, or two different adenoviral vectors, wherein one or more of the vectors encodes one or more target antigens, and then exposing the organism to a boosting step that comprises administering to the organism an adenoviral vector and a pox viral vector, or two different adenoviral vectors, wherein one or more of the vectors encodes one or more target antigens. The adenoviral vector and the pox viral vector, or the two different adenoviral vectors, may be administered as a mixture, or alternatively they may be administered separately. If administered separately the vectors may be administered at the same or different sites. The administration of each vector may be simultaneous, or substantially simultaneous, for example, within 10 minutes of each other, or the administration may be sequential. Preferably if the two vectors are administered sequentially, they are administered within at most about 7 days, 6 days, 4 days, 2 days, 24 hours or less, of each other.

The vectors used in the priming composition/step may be different to the vectors used in the boosting composition/step (heterologous prime boost). The vectors may differ in the type of adenovirus and/or pox virus used, and/or the vectors may differ in the antigen that one or more of the vectors encodes.

In an embodiment, the prime composition/step may comprise a different adenoviral vector and/or a different pox viral vector to that used in the boost composition/step. The adenoviral vector and/or the pox viral vector may differ in that they contain a different antigen and/or they may be a different type of vector. For example AdC9 may be used in one composition and AdC7 may be used in the other.

Preferably the vectors used in the prime and boost composition/step are the same (homologous prime boost). That is, the same composition/step containing the same adenoviral and pox viral vectors, or the same two different adenoviral vectors, is used for both the prime and the boost steps of the immunisation regimen. This has the advantage that only one mix of vectors is needed, which makes administration easier, less error prone and cheaper.

Preferably the boost composition/step is administered to the organism at least 2 weeks after the prime composition/step. Preferably the boost composition/step is administered to the organism at least about 3, 4, 5, 6, 7, 8, or more weeks after the prime composition/step. Preferably the boost is administered about 8 weeks after the prime.

The immunogenic efficacy of the mixture of adenoviral and pox viral vectors, or two different adenoviral vectors, may be boosted by another administration of the same or a similar mixture of vectors. A mixture may be considered similar if the strain of adenoviral vector and/or the strain of pox virus used is different in the prime to the boost. A mixture may also be considered similar if one or more of the antigens encoded by one or more of the vectors is different in the boost compared to the prime. The immunogenicity is improved when compared to a classical heterologous prime-boost regime (such as adenovirus followed by MVA with an 8-week interval) and also the protective efficacy of the vaccination which could reach 100% complete, sterile protection on the short and long term, shows a dramatic improvement. This is particularly surprising as it would have been anticipated that the boosting capacity of the vector mixture would be weak because of anti-vector immunity induced by the first immunisation with the mixture. Anti-vector immunity had been seen to be one of the greatest barriers to the widespread use of vectored vaccines. The surprising data of this invention suggest that this will be less of a problem than had been hitherto expected.

The marked immunogenicity of the viral vector mixture is all the more surprising when the following factors are considered. Firstly, it has been found and reported that mixtures of other vectors, particularly DNA vaccine vectors frequently lead to impaired immune responses to some components compared to the immunogenicity of the unmixed vectors (Sedegah et al, Gene Therapy (2004) 11:448-56). Secondly, it is known that many viruses including adenoviruses and poxviruses lead to the induction of high levels of antiviral factors such as type I interferon which often reduce the capacity of cells to be infected with other viruses. Such a reduction in infectivity would reduce immunogenicity. Thirdly, there is evidence that the kinetics of antigen expression by poxviruses and adenovirus are different and this would have been expected to impair their utility as a co-administered or mixed formulation (Geiben-Lynn, Clin Vaccine Immunol (2008) 15:691-6).

Preferably the one or more antigens are operably linked to a promoter in the vector.

Preferably the pox viral vector is an orthopox viral vector; preferably the pox viral vector used is the highly attenuated recombinant vaccinia virus MVA (modified vaccinia virus Ankara).

Preferably the pox viral vector is non-replicating or replication impaired.

The adenoviral vector may be a non-replicating or replication impaired human, simian, avian, bovine, ovine or porcine adenovirus. Preferably the adenoviral vector is a simian adenovirus. Preferably the adenoviral vector is a native strain, preferably the adenoviral vector is not a chimeric strain. In a preferred embodiment, at least one of the adenoviral vectors is a non-Ad5/Ad35 strain, preferably all adenoviral vectors used are a non-Ad5/Ad35 strain.

Preferably in embodiments of the invention where two different adenoviral vectors are used, the adenoviral vectors differ from one another in their sequence or serotype. Preferably at least one of adenoviral vectors is non-replicating or replication impaired.

Preferably the viral vectors used are non-replicating or replication impaired, this may have arisen naturally or may have been produced artificially, for example, by genetic manipulation. The terms "non-replicating" or "replication impaired" as used herein mean that the vector is not capable of replication to any significant extent in a host organism, and in particular is unable to cause serious infection in the host. The host organism is preferably a human, wherein the terms "non-replicating" or "replication impaired" mean that the vector is not capable of replication to any significant extent in normal human cells.

Preferably the (host) organism is a mammal, this may be a human or non-human mammal or a bird such as a chicken. A non-human mammal may include a horse, cow, sheep, pig, goat, dog, cat, mouse, rat, monkey or chimpanzee.

An immunogenic composition according to the invention may be used as a vaccine. Preferably the organism is a human.

In addition to their potential use as vaccines, immunogenic compositions according to the invention may be useful a) as diagnostic reagents; b) in adoptive T cell therapy protocols; and c) as a measure of immune competence of the vaccinee.

The immune response induced or amplified in an organism by an immunogenic composition of the invention, or by a method or use of the invention, may be a cellular immune response and/or a humoral immune response. If a cellular immune response is induced or amplified, the composition may, when administered to an organism, induce a T cell response against an antigen encoded by a vector in the composition. Preferably the T cell response is a CD8+ and/or a CD4+ T cell response. The CD4+ response may be a gamma interferon response. The CD8 response may be induced or amplified by using an antigen that contains a CD8 epitope. Preferably the induced T cells are polyfunctional and express multiple cytokines such as interferon-gamma, TNF-alpha and interleukin-2. Preferably the immune response is protective, that is, it serves to protect, either reduce or prevent, the organism from developing an infection or disease related to the antigen encoded by a vector in the composition.

If a humoral response is amplified or induced by a composition of the invention, preferably it is a TH1 biased antibody response to a target antigen.

The immune response may be assessed by determining antigen-specific IFNγ (IFNg) secretion levels by lymphocytes, or by assaying for other cytokines and chemokines secreted/induced in an antigen-specific manner. Other cytokines which may be secreted/induced in an antigen-specific manner include IL-2, IL-4, IL-6, IL-12, and TNF-alpha (TNFa); as well as chemokines such as MCP-1. The aforementioned methods are just some examples of how induction of the cellular immune system may be monitored, and are not intended to be exhaustive.

The humoral response may be assessed by determining levels of antibodies, such as, IgG1, IgG2a, overall IgG and/or IgA.

It has been surprisingly found that a composition according to the invention, comprising an adenonvirus and a pox virus vector, or two different adenoviral vectors, results in a dramatic improvement in the immunogenicity of the antigen encoded by one or more of the virus vectors. The improvement observed is further enhanced when the adenovirus and pox virus vectors, or two different adenoviral vectors, are administered together in a prime boost regimen.

The immune response may be directed to a pathogen or a cancer. The pathogen may be infectious.

The one or more antigens encoded by the viral vectors may be derived from a pathogen, such as a virus, bacterium, parasite or a fungus, or from a disease, such as cancer. For example, one or more of the antigens encoded by the viral vectors may be a protein or polypeptide or epitope derived from one or more of the following pathogens: viruses such as HIV type 1 and 2 (HIV-1 and HIV-2 respectively), Human T Cell Leukaemia Virus types 1 and 2 (HTLV-1 and HTLV-2 respectively), Herpes Simplex Virus types 1 and 2 (HSV-1 and HSV-2 respectively), a picornavirus, a hepadnavirus, a flavivirus, human papilloma virus, Lassa fever virus, HBV, HCV, EBV, CMV, foot and mouth disease virus, Epstein Barr virus, orthomyxoviruses such as influenza virus; Bacteria such as *Treponema pallidum, Neisseria gonorrhoea, Neisseria menigitidis, Staphylococci, Streptococcal* species, *M. tuberculosis, Chlamydia trachomatis* or *Haemophilus influenzae*, Parasites such as *Toxoplasma gondii, Leishmania, Theileria* and *Plasmodial* species; and fungal pathogens such as *Candida albicans*. Alternatively, or additionally, one or more of the antigens may be a cancer antigen or epitope, a measles, mumps and/or rubella antigen or epitope, a tetanus antigen or epitope, a diphtheria antigen or epitope, an Ebola antigen or epitope, a hepatitis A, B or C antigen or epitope, a polio antigen or epitope and/or an antigen or epitope relating to any other disease. In one embodiment, one or more of the antigens is not derived from HIV, in another embodiment, none of the antigens are derived from HIV.

The one or more antigens or epitopes may be derived from bacteria selected from the list comprising *mycobacteria, pneumococci, meningococci, Burkholderia, shigella* and *salmonella*.

The one or more antigens or epitopes may be derived from an organism that causes a parasitic disease, this includes *plasmodia, theileria, schistosomes, lesishmania* and *eimeria*.

A cancer antigen or epitope may include or be part of a human heat shock protein or a tumour associated antigen, such as, CEA, PSA, Muc 1 and Her2neu. The cancer antigen or epitope may be derived from one or more of the following cancers, lung, breast, kidney, colon, rectum, bone, brain, thyroid and haemoatological malignancies, such as leukaemias and lymphomas.

The one or more target antigens encoded by each vector may be the same or different.

The method of the invention may be used to immunise against diseases in which T cell responses play a protective role. Such diseases include, but are not limited to, malaria, infection and/or disease caused by the viruses HIV, herpes simplex, herpes zoster, hepatitis C, hepatitis B, influenza, Epstein Barr virus, measles, dengue, and HTLV-1; infection and/or disease caused by the bacterium *Mycobacterium tuberculosis* or *Listeria* spp; infection and/or disease caused by encapsulated bacteria such as *streptococcus, staphylococci, meningococci* and *haemophilus*; infection and/or disease caused by parasites such as *Leishmania, Toxoplasma* and *Trypanosoma*. The method of the invention may also be used to immunise against certain forms of cancer, for example, melanoma, lymphomas and leukaemias, cancers of the lung, breast and colon, or against other diseases. In one embodiment, the disease which the method of the invention may be used to immunise against may be a disease not caused by HIV. In another embodiment the disease is a disease caused by HIV.

Preferably the immunogenic or vaccine composition is for use in therapeutic or prophylactic treatments or both.

The immune response elicited by any method of the invention may be therapeutic or prophylactic or both.

An immunogenic or vaccine composition according to the invention may be for oral, systemic, parenteral, topical, mucosal, intramuscular, intravenous, intraperitoneal, intradermal, subcutaneous, intranasal, intravaginal, intrarectal, transdermal, sublingual, inhalation or aerosol administration.

A composition according to the invention may be administered to a subject/organism in the form of a pharmaceutical composition. In addition to the immunogenic or vaccine composition, a pharmaceutical composition preferably comprises one or more physiologically and/or pharmaceutically effective carriers, diluents, excipients or auxiliaries which facilitate processing and/or delivery of the antigen and/or adjuvant.

Determination of an effective amount of an immunogenic or vaccine composition for administration to an organism is well within the capabilities of those skilled in the art. For example, for mouse to humans, a DNA vaccination dose may comprise from about 0.1 µg to about 10 mg. For an adenoviral vector the vaccination dose may be between about $1\times10^5$ and about $1\times10^{16}$ viral particles per animal, preferably between about $1\times10^5$ and about $1\times10^{13}$ viral particles per animal. For an MVA vector the vaccination dose may be between about $1\times10^2$ and about $1\times10^{10}$ pfu per animal, preferably between about $1\times10^5$ and about $1\times10^9$ pfu per animal.

The ratio of the MVA vector amount (in pfu) to the adenovirus vector amount (in viral particles—vp) may be of any ratio, but preferably in the range 10:1 to 1:10$^6$, and most preferably in the range of a ratio of 1:10 to 1:10,000.

A composition according to the invention may be administered with a non-vectored adjuvant.

A composition according to the invention may be used in isolation, or it may be combined with one or more other immunogenic or vaccine compositions, and/or with one or more other therapeutic regimes. The method or composition of the invention may be used in combination with other immunogenic compositions, such as, compositions containing dead or inactivated organisms or purified products derived therefrom.

According to a further aspect the invention provides a kit for use in inducing an immune response in an organism, comprising an immunogenic or vaccine composition according to the invention and instructions relating to administration. The adenoviral vector and the pox viral vector, or the two different adenoviral vectors, may be provided in the kit as a mixture in the same composition, or they may be provided as separate compositions, which are mixed before use or administered separately. Where the vectors are for separate administration, the kit may include instructions to administer the vectors simultaneously, or substantially simultaneously, for example, within 10 minutes of each other, or the administration may be sequentially. Preferably if the two vectors are administered sequentially, they are administered within at most about 7 days, 6 days, 4 days, 2 days, 24 hours or less, of each other.

According to a yet further aspect, the invention provides a pharmaceutical composition comprising an immunogenic or a vaccine composition according to the invention and one or more physiologically effective carriers, diluents, excipients or auxiliaries.

According to another aspect, the invention provides the use of an immunogenic composition according to the invention in the preparation of a medicament for the treatment and/or prevention of infection and/or disease related to one or more of the antigens encoded by one or more of the vectors in the immunogenic composition.

Where the one or more antigens encoded by the one or more vectors in the composition is from a pathogen, the medicament may be intended/used to confer protection from infection and/or from disease caused by the pathogen from which the antigen of interest is derived. Alternatively, where the antigen is a cancer antigen or an antigen associated with a particular disease, the medicament may be intended/used to confer protection from, and/or to treat, the cancer or the particular disease from which the antigen is derived.

The medicament or composition may be a vaccine.

According to another aspect the invention provides the use of an immunogenic composition according to the invention in the treatment and/or prevention of infection or disease related to the antigen encoded by a vector in the immunogenic composition.

Preferably, in a use according to the invention the composition or medicament induces an immune response when administered to an organism.

According to yet another aspect the invention provides a kit comprising (i) a priming composition comprising an adenoviral vector and a pox viral vector, or two different adenoviral vectors, wherein one or more of the vectors encodes one or more target antigens; (ii) a boosting composition comprising an adenoviral vector and a pox viral vector, or two different adenoviral vectors, wherein one or more of the vectors encodes one or more target antigens; (iii) instructions to administer the priming composition and boosting composition with an interval of least two weeks.

Again the adenoviral vector and the pox viral vector, or the two different adenoviral vectors, may be provided in the kit as a mixture in the same composition, or they may be provided as separate compositions, which are mixed before use or administered separately. Where the vectors are for separate administration, the kit may include instructions to administer the vectors simultaneously, or substantially simultaneously, for example, within 10 minutes of each other, or the administration may be sequentially. Preferably if the two vectors are administered sequentially, they are administered within at most about 7 days, 6 days, 4 days, 2 days, 24 hours or less, of each other.

The priming and boosting compositions are preferably identical.

In step (iii) the interval may be at least 3, 4, 5, 6, 7, 8 or more weeks.

Preferably, in all aspects of the invention, both the adenoviral vector and the pox viral vector, or both the different adenoviral vectors, encode one or more target antigens.

According to any aspect of the invention, the adenoviral vector and pox viral vector, or two different adenoviral vectors, may be administered at different sites of the body, or by different routes (for example, intramuscular route and intradermal route). The adenoviral vector and pox viral vector, or two different adenoviral vectors, may be simultaneously administered at different sites, or by different routes.

The skilled man will appreciate that any of the preferable features discussed above can be applied to any of the aspects of the invention.

BRIEF DESCRIPTION OF THE FIGURES

Preferred embodiments of the present invention will now be described, merely by way of example, with reference to the following figures and examples.

FIG. 1A includes pie charts showing a comparison of the cytokine profile between the Ad+M, Ad and MVA regimes in relative numbers (Colour codes in pie charts: Light gray=single producers of IFNg only, Dark gray=production of two cytokines, IFNg and TNFa; Black=production of the three cytokines, IFNg, TNFa and IL2). Colour codes for bar charts: Black=AdC9; dark grey=AdC9+MVA; light grey=MVA. The bar charts in FIG. 2A show a comparison in absolute numbers. Note that the dark grey bars (Ad+M) are significantly higher than the black (Ad) and light grey (MVA) for the 2+ cytokine producers. FIG. 2B shows the absolute number of multifunctional 3+ cells taken and magnified from the bar chart from FIG. 2A, in order to visualize the absolute number of cells producing three cytokines, which due to the scale in FIG. 2A is difficult to see.

FIGS. 3A and 3B—show a comparison of immunogenicity and protective efficacy of a single prime with Ad+M to a prime-boost regime A-M. BALB/c mice were vaccinated with either a mixture of two vectors (a single application of AdC9, $5 \times 10^9$ vp+MVA, $1 \times 10^6$ pfu in the same prep) or a prime-boost regime (prime: AdC9, $5 \times 10^9$ vp and a boost after 8 weeks with MVA, $1 \times 10^6$ pfu). In FIG. 3A the immune responses were assessed by ELISpot on week 2 and 8 after the last vaccination, and in FIG. 3B survival to a challenge was assessed at the same time points.

FIGS. 4A, 4B and 4C—show the immunogenicity of prime-boost regimes using the Ad and MVA vectors individually (A-M) or in combination (Ad+M). BALB/c mice were immunized with AdC9ME.TRAP ($5 \times 10^9$ vp) and MVA ME.TRAP ($1 \times 10^6$ pfu) individually (Ad-MVA) or mixed in the same prep (Ad+MVA). Mice were boosted 8 weeks later with only MVA (after AdC9) or combination of vectors in a homologous (AdC9+MVA) or heterologous (AdC7+MVA) regime after the initial AdC9+MVA. The immune responses were assessed by ELISpot at either, 2 (FIG. 4A) and 8 (FIG. 4B) weeks after the last vaccination. Of all the regimes, both prime-boost with Ad+M mixed vectors were the most immunogenic on the short term, whereas the homologous Ad+M regime was the most immunogenic on the long term.

FIGS. 7A-D—show enhanced immunogenicity by homologous prime-boost regimes using a mixture of AdH5 and MVA vectors expressing the ME.TRAP transgene.

FIG. 8A-E—show a comparison of the immune responses to ME.TRAP by administration of mixed vectors or co-administration of two vectors in different anatomical sites and routes. FIG. 8A—BALB/c mice were immunized with a mixture of AdH5 ($5 \times 10^9$ vp/mouse) and MVA ($1 \times 10^6$ pfu/mouse) expressing ME.TRAP (left); or with the individual vectors in different ears (id route, center) or routes (AdH5 im, MVA id, right). FIG. 8B—comparison of the immunogenicity elicited by the mixture with the vectors alone, all injected intradermally; FIG. 8C—immunogenicity elicited by co-administering the vectors in different ears and its comparison with the vectors alone; FIG. 8D—immunogenicity by co-administration of the vectors using different routes (AdH5, im; MVA id) and the controls using vectors alone via the same routes. FIG. 8E—T cell responses to Pb9 upon a triple homologous immunization using a vector mixture, an intradermal and an intramuscular co-administration of both vectors.

FIG. 9A-E—show decrease in the anti-vector immunity by the vector mixtures. BALB/c mice were immunized with AdH5ME.TRAP ($5 \times 10^9$ vp/mouse), MVAME.TRAP ($1 \times 10^6$ pfu/mouse) or a mixture of AdH5+MVAME.TRAP at the same doses. Responses were assessed using an IFNg ELISpot after stimulation with a peptide (F2G) that forms part of the structure of MVA.

RESULTS

T-Cell Responses are Significantly Enhanced when Using a Combination of Adenoviral and MVA Vectors (A+M).

Figure 1A:
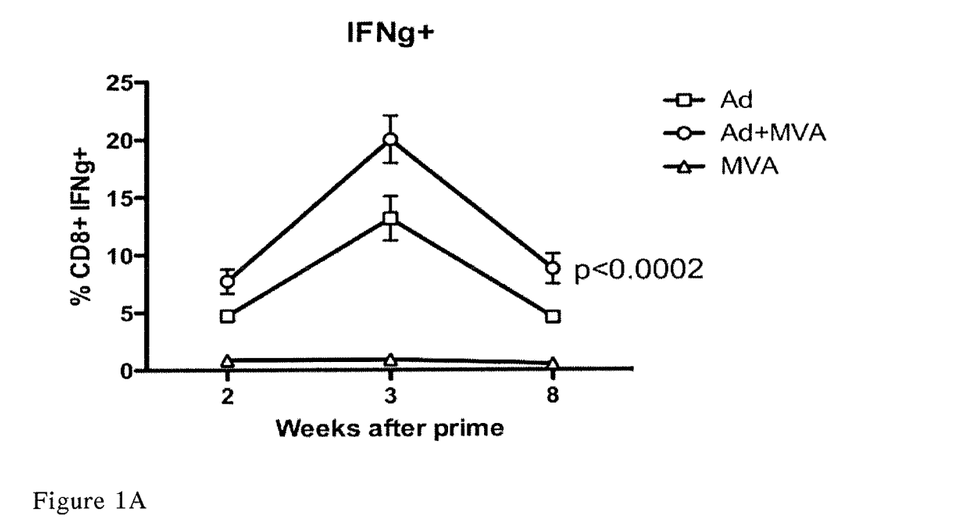
FIGS. 1A and 1B—show a comparison of the CD8$^+$ T-cell responses after vaccination of mice with a combination (Ad+MVA) vaccine and single vectors (Ad or MVA). Female BALB/c mice were immunized with AdC9 (5×10$^9$ vp), MVA (1×10$^6$ vp), or a combination of both vectors in the same prep (Ad+MVA) at the same concentration. Immune responses were assessed by flow cytometry at 2, 3 and 8 weeks post immunization. Responses were measured by the amount of IFNγ (FIG. 1A) or TNFα (FIG. 1B) produced by CD8$^+$ T cells. Note that the Ad+MVA were stronger than individual regimes at all time points measured.
Figure 1B:
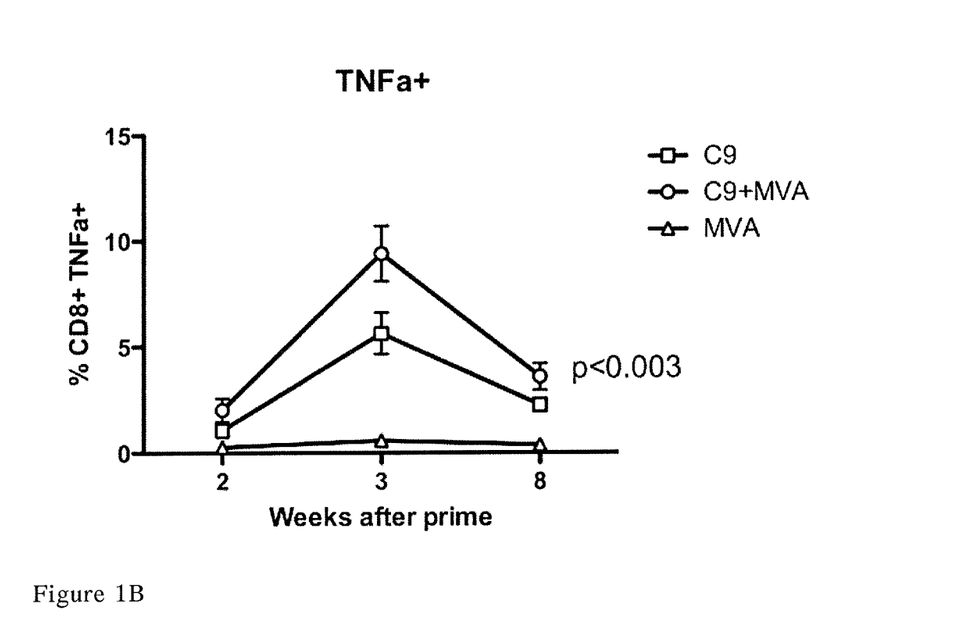

To compare the T-cell responses induced by a combination (Ad+M) vaccine to those induced by individual vectors (Ad or MVA), BALB/c mice were immunized with AdC9 ($5 \times 10^9$ vp), MVA ($1 \times 10^6$ vp), or a combination of both vectors in the same prep (Ad+MVA) at the same concentration. CD8+ T-cell responses were measured by flow cytometry at 2, 3 and 8 weeks after vaccination. As shown in FIG. 1, when both vectors, Ad+MVA were administered at the same time, the immunogenicity was significantly higher than the responses elicited by the individual vectors.

Figure 2A:
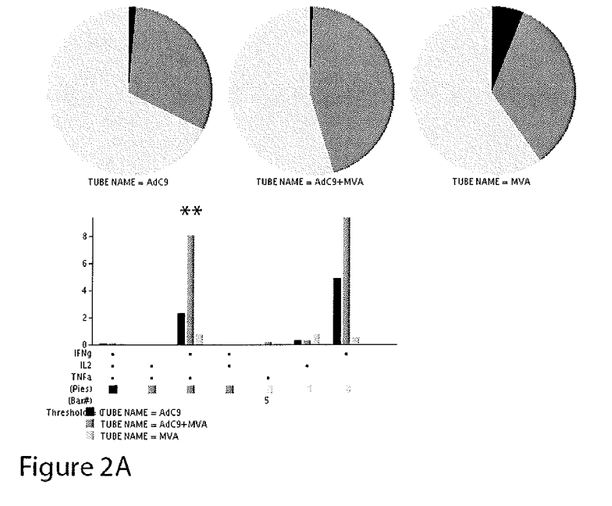
FIGS. 2A and 2B—show the multifunctional CD8$^+$ T cell responses elicited by Ad+M, Ad or M regimes upon a single immunization. Mice were immunized as described in FIG. 1 and splenocytes were co-stained for CD8, INFγ, TNFα and IL2 and analyzed by flow cytometry on week three after the immunization. The cells were assessed for co-production of the three cytokines by using a Boolean analysis in flowjo and SPICE software.
Figure 2B:
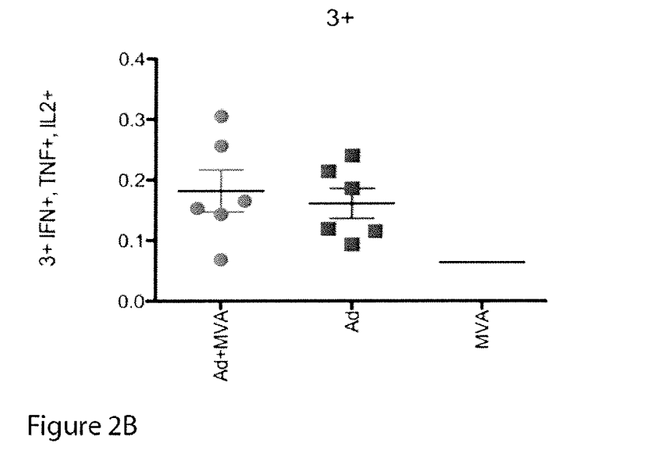

Additionally, the multifunctionality of the CD8+ responses was also analyzed in the Ad+M regime and compared to the Ad alone. It has been shown in the disease model of leishmania, where CD4+ T cells are important for protection, that better protection to disease correlates with an increased multifunctionality of T cells (Darrah, et al, Nat Med (2007) 13:843-850). As shown in FIG. 2, the combination regime not only increases the magnitude of the T-cell responses, but also the functionality, where the triple positive (3+, IFNg+, TNFa+, IL2+) and double positive (2+, IFNg+ and TNFa+) are increased (p<0.01 for the latter).

Comparison of Immunogenicity Between the Ad+M Mixture and a Prime-Boost Regime.

Figure 3A:
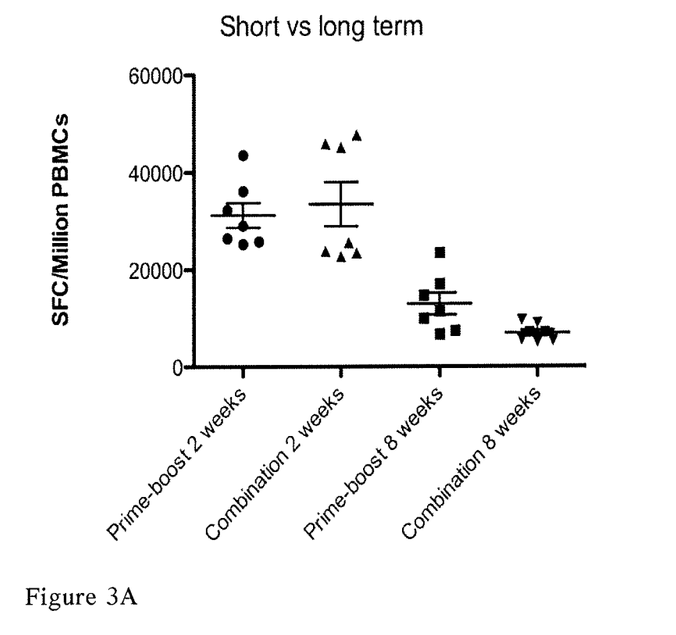
Figure 3B:
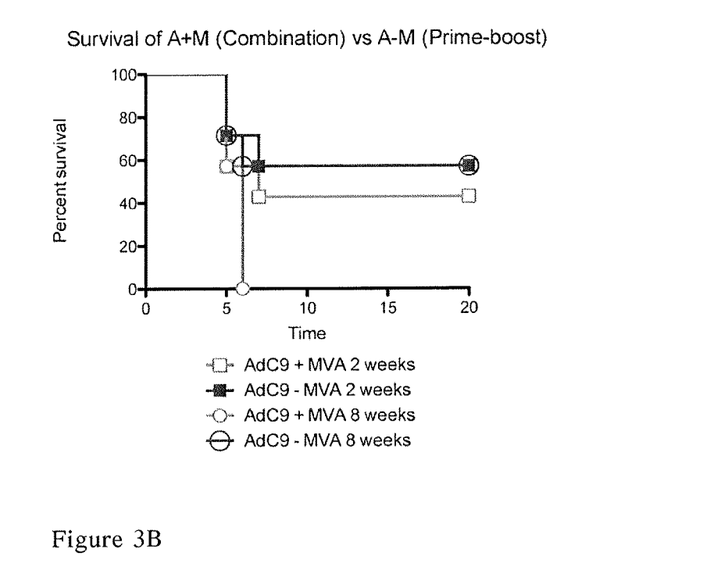

Whilst Ad vectors can elicit outstanding protection in the short term by a single immunization (Reyes-Sandoval, A., et al Eur J Immunol (2008) 38:732-741), the method of the invention using a prime boost regimen allows long-term protection. More specifically, when the vector combination is sequentially administered over a period of some time (8 weeks) the immunogenicity and protective levels are enhanced, especially over the long term after the last vaccination has been applied (Reyes-Sandoval et al, manuscript in preparation). In this example an initial prime with Ad, followed by a boost with MVA, eight weeks apart, was compared to a single prime with an A+M mixture. As shown in FIG. 3, shortly after the vaccination (single for Ad+M and double for A–M separated by 8 weeks), the numbers of CD8+ T-cells producing IFNg are similar when the two vectors are given at the same time (Ad+M) than when they are given separately in a prime-boost (A–M). However, when assessed long after the vaccination (8 weeks) the potency after the prime-boost regime was better than in an Ad+M. For both regimes, protection to malaria was also better in a prime-boost regime than with a single prime with Ad+M.

The protective efficacy of a combination regime Ad+M was also compared to a single prime with Ad, which in terms of comparing efficacy, gives a better idea of the improvement of the Ad+M over an Ad alone. Table 1 shows the results of both regimes.

TABLE 1 provides a comparison of the protective efficacy of an Ad + M regime vs Ad alone.

| Single prime | Protection 2 weeks after vaccine | Protection 8 weeks after vaccine |
|---|---|---|
| Ad | 14% | 0% |
| Ad + MVA | 43% | 0% |

Data were taken from different experiments and show a comparative result of the protective efficacy between a single administration of AdC9 (Ad) and a mixture of the two vectors (Ad + MVA)

Mixtures of Vectors Uses as Prime-Boost Regimes

Figure 4A:
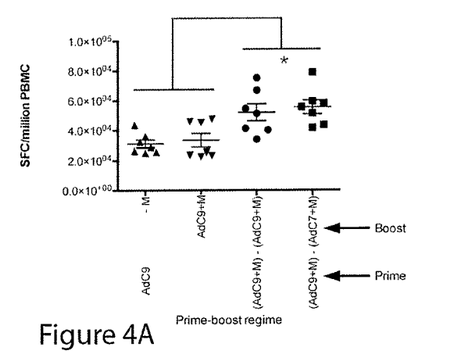
Figure 4B:
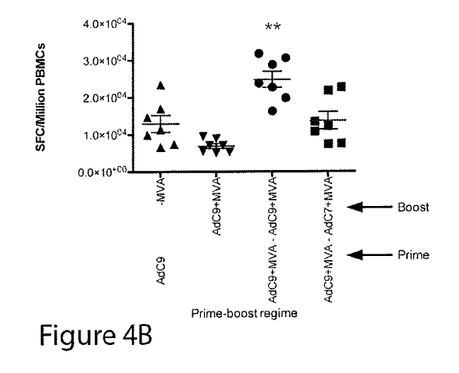
Figure 4C:
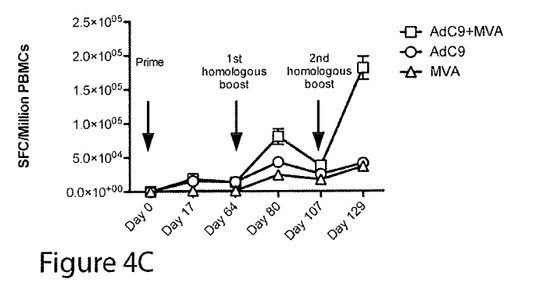
FIG. 4C shows frequencies of the T-cell responses after multiple homologous vaccinations with either, an Ad+M mixture and Ad or MVA alone. As can be seen, an AdC9+MVA mixture can be used repeatedly to enhance the T-cell responses without the need of heterologous immunizations (like a typical vaccination regimen), while repeated immunizations with Ad or MVA alone do not substantially increase immunogenicity.

To determine if the immunogenicity and protective efficacy of a combination regime (Ad+MVA) could still be improved, especially on the long term, BALB/c mice were initially primed with AdC9+MVA and subsequently boosted with another combination of vectors, either homologous (AdC9+MVA–AdC9+MVA) or heterologous (AdC9+MVA–AdC7+MVA). Such regimes were compared to the usual prime-boost with individual vectors (Ad–MVA) and a single immunization containing both vectors in the same prep (AdC9+MVA). As shown in FIG. 4, the AdC9+MVA regimes were successfully boosted either, by a homologous or a heterologous regime. The immunogenicity for the boosted mixture was significantly higher than a single administration with mixed virus (AdC9+MVA) or the prime-boost regimes. In particular, these data show the ability to enhance the T-cell responses by a homologous prime-boost, using the same Ad and MVA for the initial prime and the subsequent boost (FIG. 4, AdC9+MVA–AdC9+MVA).

Improved Protection by Prime-Boost Regimes with a Combination of Ad and MVA Vectors To test if the prime-boost regimes made with the combination of vectors could induce better protection than a prime-boost using individual vectors, the same BALB/c mice from FIG. 3 were challenged with P. berghei 2 weeks after the last vaccination.

Figure 5A:
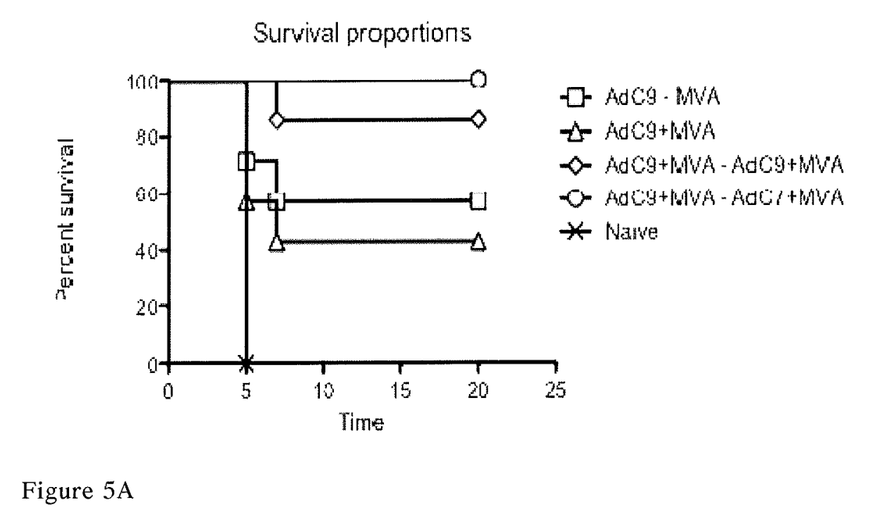
FIGS. 5A and 5B—demonstrate the enhanced protection provided by prime-boost regimes using a combination of vectors (AdC9+MVA or AdC7+MVA). Mice were immunized as described in FIG. 2. The challenge was performed by i.v. injection of 1,000 spz on week two (FIG. 5A) and on week 8 (FIG. 5B) after the last vaccination.
Figure 5B:
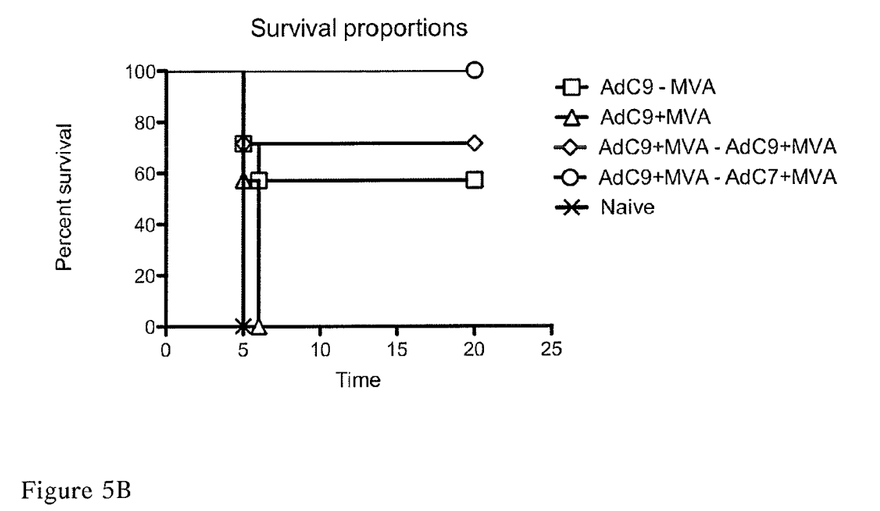

As shown in FIG. 5, the homologous and heterologous prime-boost regimes that were administered as a combination of vectors, induced outstanding levels of protection that were higher than a prime-boost with individual vectors or a single prime with a mixture.

Figure 6:
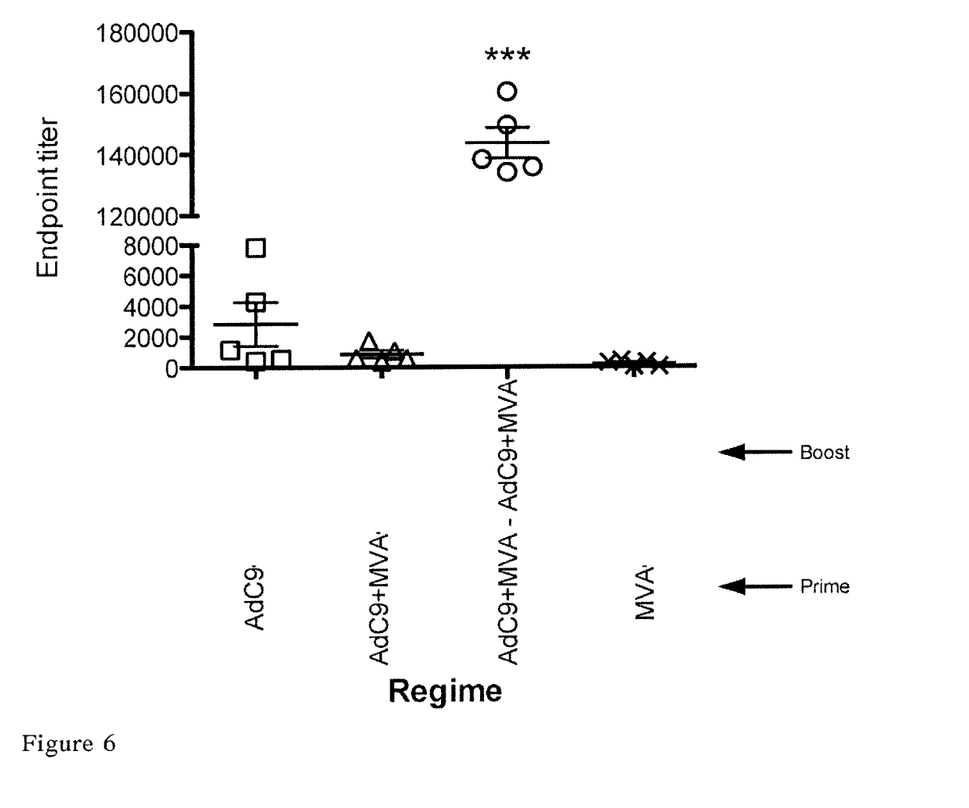
FIG. 6—shows the antibody titres produced following a single vaccination with AdC9, MVA, AdC9+MVA or a homologous prime-boost regime using individual using the mixture of vectors AdC9+MVA twice. As can be seen, antibody responses can be enhanced after an homologous boost with the Ad+MVA mixture.

In addition, FIG. 6 shows that a homologous prime-boost using the mixture of AdC9+MVA ME.TRAP can also enhance the antibody responses to TRAP. The figure shows a contrast between the antibody responses induced by a single immunization with the vectors alone (AdC9, MVA) or in a mixture (AdC9+MVA) and the antibody response induced upon a homologous prime-boost with the AdC9+MVA mixture.

A Vector Mixture Enhances Immunogenicity with Various Adenoviral Serotypes and it is not Only Specific to AdC9

To determine if the improved immunogenicity obtained by using simian adenoviral vector AdC9 mixed with MVA is a common feature induced by other adenoviruses, mice were immunized with Ad+MVA vector mixtures containing the human serotype AdH5 mixed with MVA (AdH5+MVA).

The experiment was set to assess if this mixture was more immunogenic than the vectors alone upon a prime or a homologous prime-boost. Additional arms were included to determine if a potentially improved immunogenicity would be dose-dependent and if the optimal dose could be similar to that of AdC9.

Figure 7:
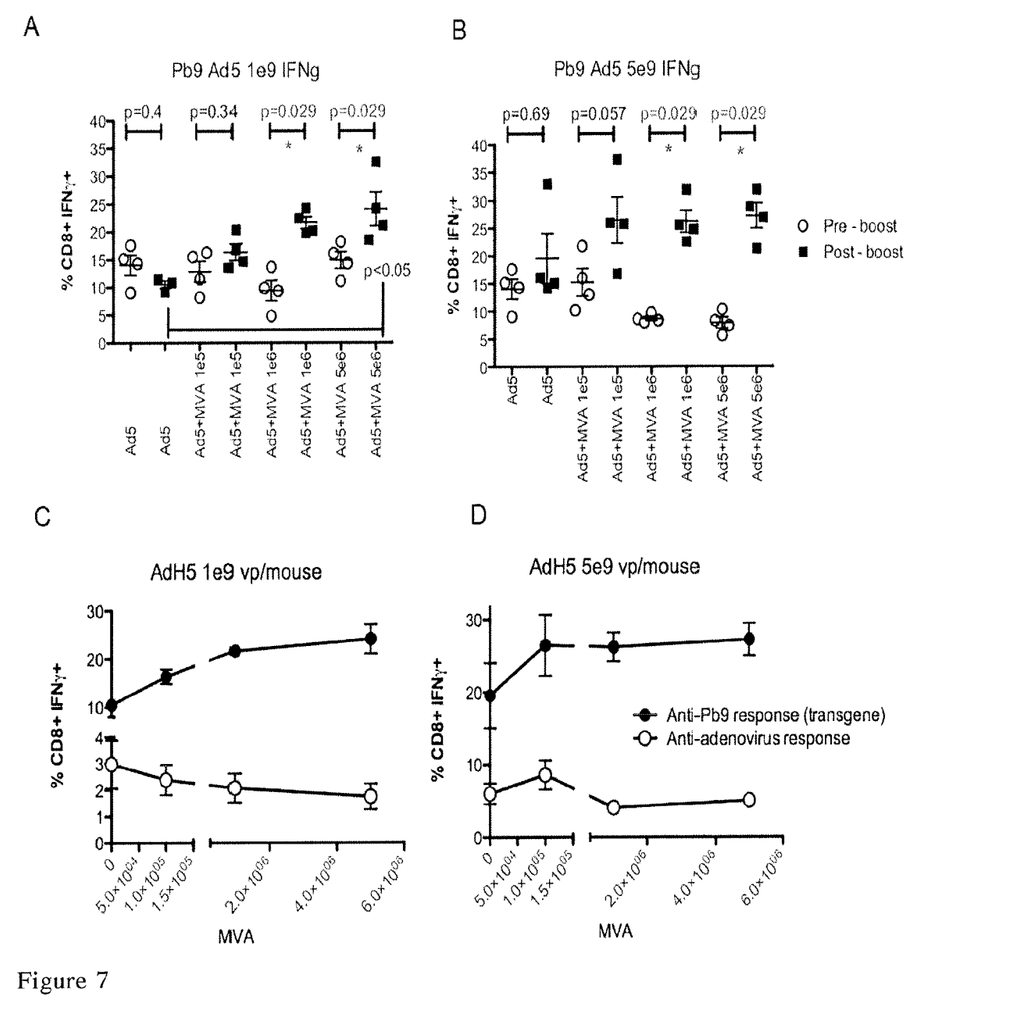
FIG. 7A—BALB/c mice were immunized intradermally with AdH5ME.TRAP ($1 \times 10^9$ vp/mouse) alone or mixed in the same prep with increasing doses of MVAME.TRAP ($1 \times 10^5$, $1 \times 10^6$ and $5 \times 10^6$ pfu/mouse). Responses to the Pb9 peptide (SYIPSAEKI) present in ME.TRAP were assessed by ELISPOT on week 10 after vaccination (open circles) and week 2 after a homologous boost with the same construct and doses (close squares).
FIG. 7B—BALB/c mice were immunized as described in A, using AdH5 (at a higher dose of $5 \times 10^9$ vp/mouse) alone or mixed with increasing doses of MVA. Immune responses were assessed as described in A.
FIG. 7C—Comparison of the anti-vector immunity to AdH5 (open circles) and the transgene-specific responses (closed circles) elicited by the immunization with AdH5 alone ($1 \times 10^9$ vp/mouse) or mixed with increased doses of MVA. Anti-Ad immunity was assessed by flow cytometry after stimulation with a combination of two peptides (KIA and ALA) present in the AdH5.
FIG. 7D—Similar to C but upon injection of higher doses of AdH5 ($5 \times 10^9$ vp/mouse).

In the experiment shown in FIG. 7A, the AdH5 dose was kept constant at $1 \times 10^9$ vp/mouse (lower than the dose used for AdC9) and MVA was administered at increasing doses ($1 \times 10^5$, $1 \times 10^6$ and $5 \times 10^6$ pfu/mouse). The immunogenicity was similar for all regimes after prime (open circles). However, upon a homologous boost (closed squares), Ad5+MVA regimes were significantly more immunogenic than Ad alone at the two highest doses of MVA tested. Importantly, Ad5 alone was not able to boost the responses, while all the mixed regimes did. Finally, a comparison amongst the responses post-boost show that only the mixture containing the highest dose of MVA ($5 \times 10^6$ pfu) is significantly higher than the homologous prime-boost with Ad5.

A similar experiment is shown in FIG. 7B. This time, a higher dose of $5 \times 10^9$ vp/mouse of AdH5 was used both, alone and mixed with MVA. Responses were similar in all groups after a single vaccination (open circles) and we can see that immunogenicity of Ad5+MVA regimes at higher doses of MVA were lower than Ad alone. A similar result to FIG. 7A was observed, in which the A+M homologous prime-boost enhanced immunogenicity when compared to Ad alone. Only the groups with highest doses of MVA in the mixture were significantly higher after boost when compared to the prime but this might be due to the fact that the priming responses in those two groups were lower than the lower MVA doses of Ad5 alone.

It can be concluded that the Ad+MVA vector mixtures can enhance the CD8 responses not only when the chimpanzee vector AdC9 is used but also with the human serotype AdH5. The enhancement of the T-cell responses was seen at two different doses of AdH5 and at three different doses of MVA, broadening the range of both vectors to be used in the mixture. Importantly, the major differences in the levels of immunogenicity were seen when a higher dose of Ad was used ($5 \times 10^9$ vp) and also at the highest doses of MVA ($1 \times 10^6$ and $5 e^6$ pfu). Finally, a mixture of Ad+MVA permits the sequential homologous boost, which is not possible when the adenoviral vector is used alone. A similar improvement of the immunogenicity and the ability to use the adenoviral vectors in homologous prime-boost regimes has also been seen when using other serotypes of adenoviral vectors mixed with either, MVA or an additional adenoviral vector.

We have also attempted to understand the reasons that allow multiple immunizations using the same adenoviral vector repeatedly. As shown in FIGS. 7C and 7D, the T-cell responses against the adenoviral vector (anti-vector immunity) has also been assessed in the same experiment and it was found that by administering the two vectors at the same time, the anti-vector immunity can be reduced and therefore allow a repeated administration of both, Ad and MVA.

Immune Responses Induced by Mixture Versus Co-Administration

An important question is whether the vectors can enhance the T-cell responses only when they are applied mixed in a single prep or if they can be co-administered in separate preps and routes simultaneously.

Figure 8:
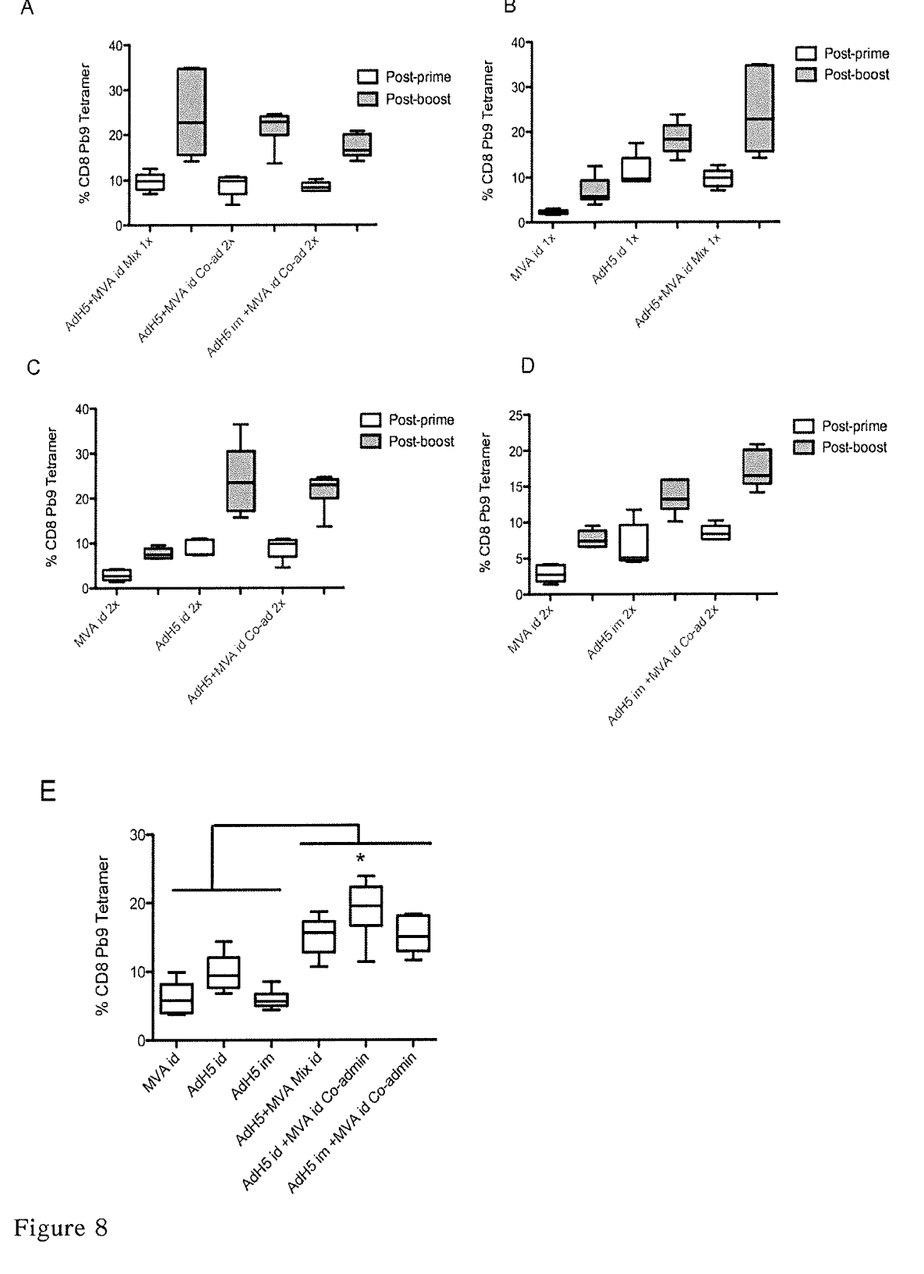

This question was addressed in an experiment in which mice were immunized with AdH5 mixed with MVA and compared immunogenicity to that of a co-administration of both vectors simultaneously but at different sites. FIG. 8A shows a comparison between different regimes. As can be seen in general all regimes were successfully boosted by a homologous immunization. Upon a boost, the vector mixture (8A, bar on the left) yielded similar immunogenicity to the co-administration intradermally (8A, center) and when the Ad vector was administered via the intramuscular route (8A, right). FIGS. 8B-D show a comparison of the immunogenicity for these three groups with their respective controls. FIG. 8B shows the immunogenicity of a vector mixture applied intradermally compared to a homologous prime-boost using both, Ad and MVA vectors alone. FIG. 8C shows that the intradermal co-administration (each vector injected into different ears) can also be boosted by a homologous vaccination but it did not improve the responses elicited by homologous prime-boost using Ad alone. The Ad vector was injected intramuscularly and co-administered with MVA intradermally (FIG. 8D), showing that such regime can also be boosted by a homologous vaccination and the immunogenicity was better than the vectors alone. Finally, upon 3 consecutive homologous vaccinations, it was found that the immunogenicity was enhanced by the three regimes that consist on the combination of vectors: mixture, intradermal and intramuscular co-administration of adenovirus and MVA.

In conclusion, this experiment shows that two vectors can be mixed or co-administered in different sites and the responses can be enhanced by homologous prime boost.

Understanding the Mechanism to Enhance Immunogenicity and Allow Homologous Prime Boost Using a Mixture of Ad+MVA Anti-Vector Immunity Some potential mechanisms by which the A+M mixture can enhance immunogenicity and also allow a homologous prime-boost have been assessed. One of the major disadvantages of the vectored vaccines, particularly those using adenoviral vectors is the potent anti-vector immunity elicited after vaccination that precludes a subsequent vaccination with the same vector.

Figure 9:
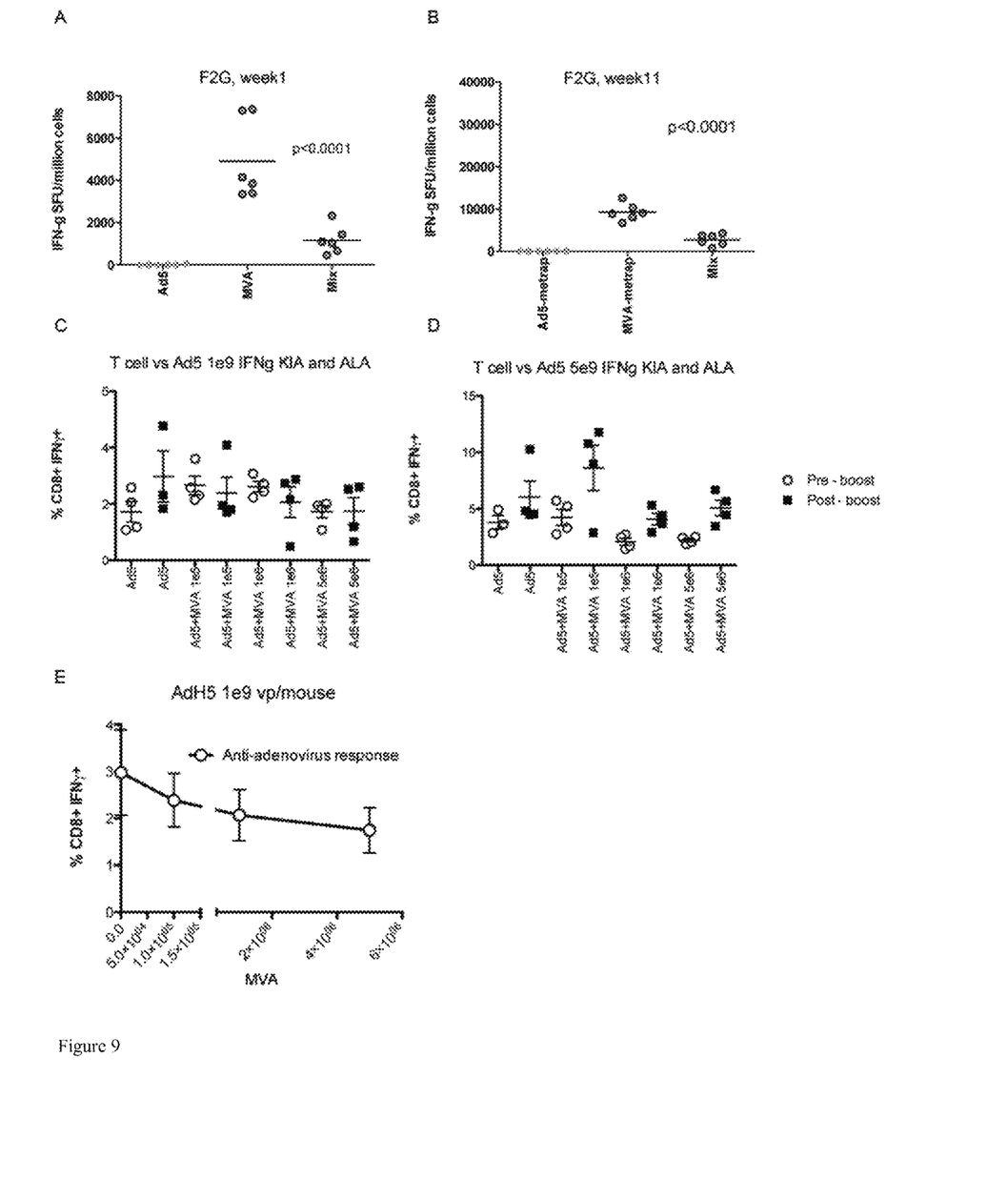
FIG. 9A—anti-MVA responses at week 1 post-vaccination.
FIG. 9B—anti-MVA responses at week 11 post-vaccination.
FIG. 9C—anti-Ad responses measured by ICS upon stimulation with the adenoviral peptides KIA and ALA. AdH5 was used at doses of $1 \times 10^9$ vp/mouse alone or in combination with increasing doses of MVA.
FIG. 9D—anti-Ad immunity was assessed using higher doses of AdH5 ($5 \times 10^9$ vp/mouse)
FIG. 9E—correlation showing a decrease of the anti-Ad responses when the MVA increases in concentration in the mixture. Graph shows responses after an homologous boost when the Ad vector is used at low doses.

Therefore, it was assessed if a vector mixture improves immunogenicity by reducing the anti-vector immunity. Blood from mice that have been vaccinated with AdH5+MVA, AdH5 and MVA all expressing ME.TRAP was assessed for the presence of T cells reacting against a sequence of the MVA vector using a stimulation with the F2G peptide. As shown in FIGS. 9A and B, there is a decreased T-cell response against MVA after immunization with a vector mixture when compared to MVA alone.

T-cell responses against the adenoviral vector (AdH5 in this case) were also assessed after immunization. Two doses of AdH5 (low: $1 \times 10^9$ vp; high: $5 \times 10^9$ vp) were used alone or in combination of various doses of MVA (No MVA, $1 \times 10^5$ pfu, $1 \times 10^6$ pfu and $5 \times 10^6$ pfu) and anti AdH5 responses were assessed using two peptides: KIA (KYSPSNVKIA (SEQ ID NO: 1)) present in the Ad hexon, on the surface of the vector and ALA (LPKLTPFALA (SEQ ID NO: 2)), present in a DNA binding protein, inside the Ad.

As shown in FIG. 9C, at low doses of AdH5, there was an increase in the anti-Ad immunity when AdH5 was used alone as a prime-boost regime. However, none of the mixed regimes with MVA showed an increase in the anti-vector immunity after a homologous boost. At higher doses of Adenovirus (FIG. 9D), all of the vaccination regimes showed an increase in the anti-vector immunity upon a boost, however, responses were lower when high doses of MVA were used in the mixture.

Improvement of Subdominant Responses by AdH5+MVA Mixture Regimes

A decrease in the anti-vector responses could also allow for other subdominant T-cell responses to be modified. In our construct, Pb9 induces a dominant T-cell response. However, it has been investigated if the sub-dominant responses against TRAP could also be enhanced by a vector mixture, which could be important due to the fact that an increase in the breadth of the responses against the transgene could enhance the protective efficacy in humans.

Figure 10:
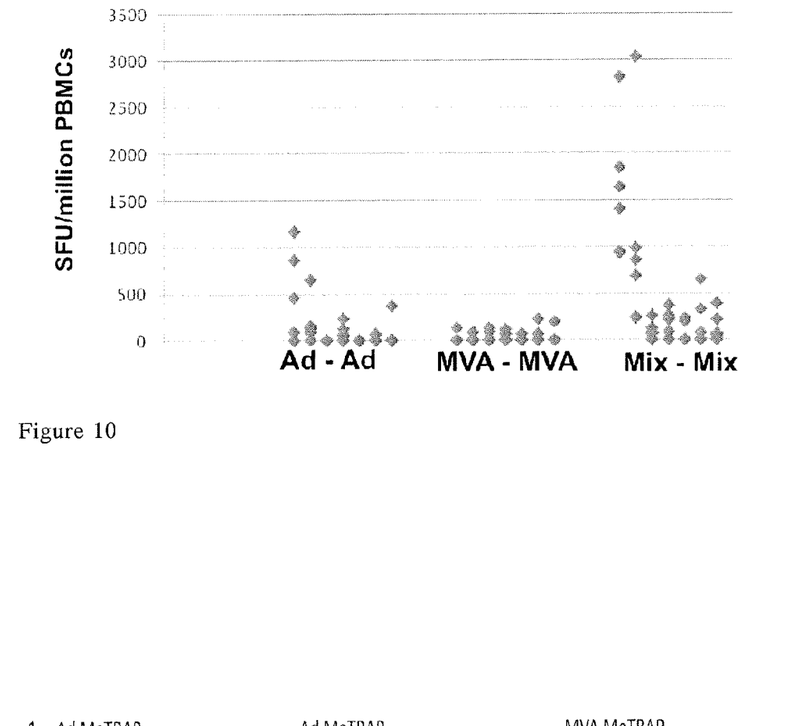
FIG. 10—shows enhancement of the sub-dominant T-cell responses by an AdH5+MVA ME.TRAP mixture. BALB/c mice were immunized using homologous prime-boost regimes with AdH5 ME.TRAP ($5 \times 10^9$ vp/mouse). MVAME.TRAP ($1 \times 10^6$ pfu/mouse) or a Mixture of AdH5+MVAME.TRAP at the same concentrations. T-cell responses were assessed using a peptide pool containing 12 peptides of the ME.TRAP transgene that induce a sub-dominant response against ME.TRAP in BALB/c mice. Positive responses were added and an overall sub-dominant response against all peptides is shown in the graph.

As shown in FIG. 10, responses to subdominant epitopes present in TRAP were enhanced when the vector mixture was used for immunization.

In summary, it is shown that a vector mixture regime can enhance a T-cell response to a transgenic protein expressed by the Ad and MVA vectors. The improvement can be seen using various serotypes of Ad vectors combined with MVA. In addition, an improvement in immunogenicity can be induced not only by the vector mixture but also by the co-administration of the Adenovirus and the MVA in separate sites and routes. The increased immunogenicity can be against the dominant peptide and the sub-dominant epitopes, which demonstrate an enhancement not only in magnitude but also in breadth of the immune response which can result in an improvement of the protective efficacy upon a vaccination with a mixture. Such results can be explained by the decrease in the anti-vector immunity towards both, the Adenovirus and the MVA vectors.

Immune Responses in Rhesus Macaques

Taking into consideration that the vector mixtures enhanced the transgene responses, it is expected that improved immunogenicity could be reproduced in bigger animals, such as a model consisting on outbred rhesus macaques.

The inbred nature of the BALB/c model makes the T-cell responses to be directed mainly against a single epitope in the ME.TRAP transgene, the Pb9. Immunising macaques would assess the immune response against the whole ME.TRAP molecule which could be a good indicator of the responses in humans.

For the study, two groups consisting of 6 rhesus macaques are immunised with homologous prime-boost regimes consisting of 1) AdCh63ME.TRAP (1.5×107 ihu which is ~8×10 e9 vp per macaque) injected two times at intervals of 8 weeks between prime and boost, followed by a third immunisation with MVA ME.TRAP at 107 ihu/macaque.

2) A mixture of AdCh63ME.TRAP+MVAME.TRAP (AdCh63 at 1.5×107 ihu/macaque and MVA ME.TRAP at 107 ihu/macaque.

Figure 11:
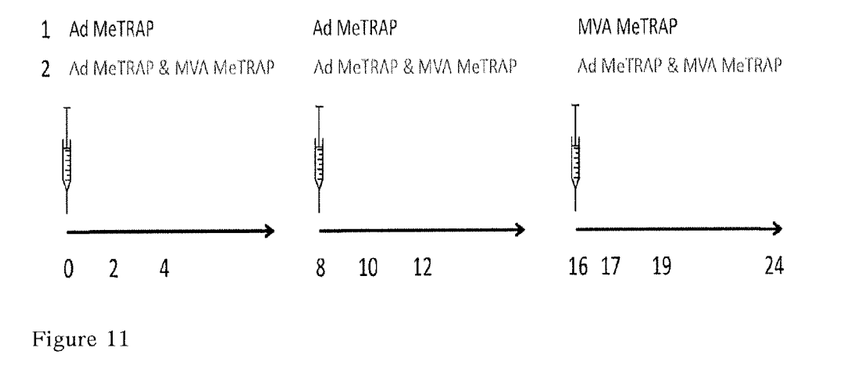
FIG. 11—illustrates a protocol to assess immunogenicity in macaques of a vector mixture consisting on an Ad+MVA. Macaques will be immunised with AdCh63ME.TRAP at a dose of $1.5 \times 107$ ihu ($\sim 8 \times 10 e^9$ vp) in intervals of 8 weeks. The Ad+MVA mixture contained a similar dose of Ad to the control group and additionally $10^7$ ihu (infection units) of MVAME.TRAP.

Immune responses can be screened by ELISpot at 2 and 4 weeks after the first and second vaccination and 1 and 3 weeks after the third vaccination (FIG. 11). A heterologous boost for group 1 can also be applied, which will consist of MVA ME.TRAP. This is expected to be a highly immunogenic regime and will serve as comparison with a homologous prime-boost immunisation.

Vaccine-specific adverse effects can be determined for any of the macaque groups. So far, no side effects have been seen in any of the mice immunized with a mixture of vectors.

Immune Responses in Humans

It can be determined if the Ad+MVA mixtures can also show good immunogenicity in humans and the protective efficacy that such regimes can elicit.

In a trial, a vector mixture can be used to vaccinate the following groups:

Group 1-4 Volunteers

Mixture formulation of AdCh63 ME-TRAP+MVA ME-TRAP

Vaccine 1: Mixture formulation on enrolment into the trial
Vaccine 2: Mixture formulation 8 weeks later
Vaccine 3: Mixture formulation 8 weeks later
Malaria Challenge: 3 weeks after last vaccination.

Group 2-4 Volunteers

Mixture formulation of AdCh63 ME-TRAP+MVA ME-TRAP

Vaccine 1: Mixture formulation on enrolment into the trial
Vaccine 2: Mixture formulation 8 weeks later
Malaria Challenge: 3 weeks after last vaccination.

Group 3-4 Volunteers

Mixture formulation of AdCh63 ME-TRAP+MVA ME-TRAP

Vaccine 1: Mixture formulation on enrolment into the trial
Vaccine 2: Mixture formulation 4 weeks later
Vaccine 3: Mixture formulation 4 weeks later
Malaria Challenge: 3 weeks after last vaccination.

This study can provide results in terms of safety, immunogenicity and protective efficacy of the AdCh63 ME.TRAP+MVA ME.TRAP vector mixture.

In terms of safety, the vector mixture is expected to be safe. The immunogenicity levels are expected to increase upon sequential boosts.

Materials and Methods

Immunization of Mice

Female BALB/c mice 6 to 8 week of age were purchased from the Biomedical Services Unit at the John Radcliffe Hospital, Oxford with all animals undertaken in accordance with the terms of the U.K. Home Office Animals Act Project License. Immunizations were performed intradermally, which has previously been shown to elicit better immunogenicity when compared to other routes e.g. sub-cutaneous, intramuscular. Adenoviruses were administered at a dose of $1 \times 10^{10}$ viral particles (v.p.) for experiments involving a single prime and lower doses of $5 \times 10^9$ vp for prime-boost protocols. MVA was used at a dose of $1 \times 10^7$ pfu for boosting the T-cell responses. All vectors were resuspended in endotoxin-free PBS prior to immunization.

Viral Vectors

All viral vectors used in the experiments, v.gr. AdC7, AdC9, AdH5 and MVA express the transgene ME.TRAP that has been previously described (Reyes-Sandoval, A., et al Eur J Immunol (2008) 38:732-741; Xiang, Z., et al J Virol (2002) 76:2667-2675; Xiang, Z. et al Virology (1996) 219:220-227). The insert ME.TRAP is a hybrid transgene of 2398 bp encoding a protein of 789 aa. The ME string contains the BALB/c H-2$K^d$ epitope Pb9 amongst a number of other B- and T-cell epitopes.

Ex Vivo IFNγ ELISPOT

ACK-treated splenocytes or PBMCs were cultured for 18-20 hours on IPVH-membrane plates (Millipore) with the immunodominant H-2$K^d$-restricted epitope Pb9 (SYIP-SAEKI) at a final concentration of 1 μg/ml. ELISPOT was performed as previously described (Reyes-Sandoval, A., et al Eur J Immunol (2008) 38:732-741).

Intracellular Cytokine Staining

ACK-treated splenocytes were incubated for 5 hours in the presence of 2 μg/ml Pb9 and 2 μl/ml Golgi-Plug (BD). To assess the liver responses, T-cells were isolated from the liver after incubation for 1 hour at 37° C. in FCS-free RPMI-1640 medium (with Gln and pen/strep), containing DNase at a final concentration of 30 mg/ml (Sigma) and collagenase at 0.7 mg/ml (Sigma). The reaction was stopped using RPMI 10% FCS and after washing, mononuclear cells were purified with Ficoll-Paque Premium (GE healthcare) and stimulated as described above.

Phenotypic analysis of CD8$^+$ T cells was performed by intracellular cytokine staining (ICS) using the antibody clones that have been described earlier (Reyes-Sandoval, A., et al Eur J Immunol (2008) 38:732-741). For tetramer staining, Pb9 peptide (Proimmune, UK) was sent to the NIH tetramer facility for synthesis (MHC tetramer core facility, Emory University Vaccine Center, Atlanta, USA). Flow cytometric analyses were performed using a FACSCanto and an LSRII (BD Biosciences). Data were analyzed with either FACSDiva (BD) or Flow Jo (Tree Star) software. Analysis of multifunctional CD8$^+$ T-cell responses was performed using a Boolean analysis in FlowJo software, Pestle and SPICE 4.0 kindly provided by M. Roederer (NIH, Bethesda).

Antibody Responses

IgG antibodies against the TRAP region were analyzed by ELISA in plates that were coated with the TRAP antigen. Serum samples were taken 3 weeks after vaccination. Serial dilutions were made in coated plates. Titres are reported as the dilution required to reach an O.D. similar to naïve serum.

Parasite Challenge

*Plasmodium berghei* (ANKA strain clone 234) sporozoites (spz) were isolated from salivary glands of female *Anopheles stephensi* mosquitoes. Parasites were resuspended in RPMI-1640 medium with each mouse receiving a total of 1,000 spz via the i.v. route. Blood samples were taken on daily basis from day 5 to 20; smears were stained with Giemsa and screened for the presence of schizonts within the red blood cells. Survival was defined as complete absence of parasites in blood.

Statistical Analysis

Statistical significance of flow cytometry samples were analyzed with either a one or two-way ANOVA and a Bonferroni post-test. All statistic tests were performed using GraphPad Prism version 4.03 for Windows, GraphPad Software, San Diego Calif., USA.

The invention claimed is:

1. A method of inducing an immune response in an organism comprising the step of administering to the organism an adenoviral vector and a pox viral vector, wherein both of the vectors encode a same target antigen and the adenoviral vector and pox viral vector-are administered simultaneously, or substantially simultaneously.

2. The method of claim 1, wherein the adenoviral vector and the pox viral vector are in the same composition.

3. The method of claim 1, wherein the adenoviral vector and the pox viral vector are in different compositions.

4. The method of claim 1, wherein the adenoviral vector and pox viral vector are administered at different sites of the body, or by different routes.

5. The method of claim 1, wherein the method is a priming step, and wherein the method further comprises the step of administering to the organism a boost comprising an adenoviral vector and a pox viral vector wherein one or more of the vectors encodes one or more target antigens, and wherein the priming step is administered before the boosting step.

6. An immunogenic composition comprising an adenoviral vector and a pox viral vector, wherein both of the vectors encode a same target antigen.

7. The composition of claim 6, wherein the pox viral vector is an orthopox viral vector or a modified vaccinia virus Ankara (MVA).

8. The composition of claim 6, wherein the adenoviral vector is of human, simian, ovine, bovine, porcine or avian origin.

9. The composition of claim 6, wherein the pox viral vector and/or the adenoviral vector is non-replicating or replication impaired.

10. A kit comprising (i) a priming composition comprising an adenoviral vector and a pox viral vector, wherein both of the vectors encode a same target antigen; (ii) a boosting composition comprising an adenoviral vector and a pox viral vector, wherein one or more of the vectors encodes one or more target antigens; (iii) instructions to administer the priming composition and the boosting composition to an organism with an interval of least 7 days.

11. The method of claim 1, wherein the pox viral vector is an orthopox viral vector or a modified vaccinia virus Ankara (MVA).

12. The method of claim 1, wherein the adenoviral vector is of human, simian, ovine, bovine, porcine or avian origin.

13. The method of claim 1, wherein the pox viral vector and/or the adenoviral vector is non-replicating or replication impaired.

* * * * *

```
                          SEQUENCE LISTING

<160> NUMBER OF SEQ ID NOS: 2

<210> SEQ ID NO 1
<211> LENGTH: 10
<212> TYPE: PRT
<213> ORGANISM: Artificial Sequence
<220> FEATURE:
<223> OTHER INFORMATION: peptide derived from Adenovirus

<400> SEQUENCE: 1

Lys Tyr Ser Pro Ser Asn Val Lys Ile Ala
1               5                   10

<210> SEQ ID NO 2
<211> LENGTH: 10
<212> TYPE: PRT
<213> ORGANISM: Artificial Sequence
<220> FEATURE:
<223> OTHER INFORMATION: peptide derived from Adenovirus

<400> SEQUENCE: 2

Leu Pro Lys Leu Thr Pro Phe Ala Leu Ala
1               5                   10
```